United States Patent
Klemm et al.

(10) Patent No.: US 10,227,335 B2
(45) Date of Patent: Mar. 12, 2019

(54) PREPARATION OF SUFENTANIL CITRATE AND SUFENTANIL BASE

(71) Applicant: Mallinckrodt LLC, Hazelwood, MO (US)

(72) Inventors: George Helmut Klemm, Hazelwood, MO (US); Brian Orr, Hazelwood, MO (US); Joel McClenaghan, Hazelwood, MO (US)

(73) Assignee: SpecGX LLC, Webster Groves, MO (US)

( * ) Notice: Subject to any disclaimer, the term of this patent is extended or adjusted under 35 U.S.C. 154(b) by 0 days.

(21) Appl. No.: 15/164,483

(22) Filed: May 25, 2016

(65) Prior Publication Data

US 2016/0347743 A1    Dec. 1, 2016

Related U.S. Application Data

(60) Provisional application No. 62/166,911, filed on May 27, 2015.

(51) Int. Cl.
*C07D 409/06* (2006.01)
*C07C 51/41* (2006.01)

(52) U.S. Cl.
CPC .......... *C07D 409/06* (2013.01); *C07C 51/412* (2013.01)

(58) Field of Classification Search
CPC .................................................. C07D 409/06
See application file for complete search history.

(56) References Cited

U.S. PATENT DOCUMENTS

| | | | |
|---|---|---|---|
| 3,998,834 A | 12/1976 | Janssen | |
| 4,179,569 A * | 12/1979 | Janssen | C07D 207/333 546/223 |
| 5,039,804 A * | 8/1991 | Feldman | C07D 471/10 546/20 |
| 5,489,689 A * | 2/1996 | Mathew | C07D 211/66 546/242 |
| 7,074,935 B2 | 7/2006 | Mathew | |
| 7,208,604 B2 | 4/2007 | Mathew | |
| 8,299,258 B2 | 10/2012 | Buenger | |
| 2002/0106410 A1 | 8/2002 | Masters | |
| 2003/0152500 A1 * | 8/2003 | Dalziel | A23J 3/16 422/245.1 |
| 2010/0010031 A1 | 1/2010 | Yum | |
| 2010/0056574 A1 * | 3/2010 | Cheng | C07D 409/06 514/326 |
| 2010/0137604 A1 | 6/2010 | Buenger | |
| 2012/0071659 A1 * | 3/2012 | Orr | C07D 409/06 546/213 |

FOREIGN PATENT DOCUMENTS

| | | | | |
|---|---|---|---|---|
| CN | 102060753 A | * | 5/2011 | |
| EP | 2455377 B1 | | 7/2014 | |
| WO | 2008/005423 A1 | | 1/2008 | |
| WO | WO 2008005423 A1 | * | 1/2008 | .......... C07D 409/06 |
| WO | 2016/191472 A1 | | 12/2016 | |

OTHER PUBLICATIONS

Stahl "Handbook of Pharmaceutical Salts: Properties Selection and Use" Verlag Helvetica Chimica Acta: 2002, pp. 191-211.*
Gattermann, Ludwig the Practical Methods of Organic Chemistry 1896, Macmillan: London, pp. 1-14.*
Zubrick, James W. The Organic Chem Lab Survival Manual: A Student's Guide to Techniques 4th Ed. 1997, Wiley: New York, pp. 121-125.*
Kubota "Seeding Effect on Product Crystal Size in Batch Crystallization" Journal of Chemical Engineering of Japan, 2002, vol. 35, No. 11. pp. 1063-1071.*
Flick "Hydrocarbon Solvents" in Industrial Solvents Handbook 1998 Fifth Edition, Noyes Data Corporation: New Jersey, pp. 3-37.*
Morrison, K. "Physical Science Level 3" Pearson Education: Capetown, 2008, pp. 16-18.*
International Search Report and Written Opinion dated Aug. 29, 2016 from related international application No. PCT/US2016/034091, 9 pgs.

* cited by examiner

*Primary Examiner* — David K O'Dell

(57) ABSTRACT

Provided herein are processes for forming sufentanil citrate from sufentanil base. One process comprises forming sufentanil citrate in the presence of a polar non-aqueous solvent. Other processes comprise forming sufentanil citrate in the presence of water.

4 Claims, No Drawings

PREPARATION OF SUFENTANIL CITRATE AND SUFENTANIL BASE

CROSS-REFERENCE TO RELATED APPLICATIONS

This application claims the priority of U.S. Provisional Application Ser. No. 62/166,911, filed May 27, 2015, the disclosure of which is incorporated herein in its entirety.

FIELD OF THE INVENTION

The present invention generally relates to the preparation of sufentanil salts and free base.

BACKGROUND OF THE INVENTION

Sufentanil is a member of the series of potent fentanyl analogs. It has a high selectivity and affinity (approximately 10 times greater than fentanyl) for "mu" opiate receptors. When compared with fentanyl, sufentanil's pharmacokinetic profile shows a smaller volume of distribution, resulting in a terminal half-life intermediate between alfentanil and fentanyl. Additionally, sufentanil, like fentanyl, does not cause histamine release. The chemical name for sufentanil is N-[4-(methoxymethyl)-1-[2-(2-thienypethyl]-4-piperidinyl]-N-phenylpropanamide. In its citrate form, the chemical name is N-[4-(methoxymethyl)-1-[2-(2-thienypethyl]-4-piperidinyl]-N-phenylpropanamide, 2-hydroxy-1,2,3-propanetricarboxylate.

The classical approach for preparing sufentanil citrate involves forming the salt from sufentanil base with citric acid (using an approximate 1:1 ratio) in water with charging everything upfront. Unfortunately, this approach leads to the salt oiling out of solution and later crystallizing. This prior process also presents several other problems. First, considerable manual intervention is required to remove the aggregated product from the sidewalls of the reactor after the oiled-out product crystallizes. The uncontrolled crystallization causes the product to solidify into chunks that must be sieved or milled to obtain to a powder fine enough for pharmaceutical formulation. Milling of such a potent compound also is extremely hazardous and raises exposure issues. Furthermore, a polishing sterile filtration is not possible since the reaction does not go through a homogeneous phase. Single step reprocessing is also not possible (e.g., the material does not redissolve in the matrix). If the sufentanil citrate product fails specifications (e.g., assay, HPLC, particulate matter, etc.), the salt must be returned to the base form and the citrate crystallization process must be repeated from the beginning. A need therefore exists for an improved salt formation and isolation method to address the latter problems.

SUMMARY OF THE INVENTION

Briefly, therefore, one aspect of the present disclosure encompasses a process for forming sufentanil citrate from sufentanil base in the presence of a polar non-aqueous solvent. The process comprises (a) contacting sufentanil base with a polar non-aqueous solvent to form a mixture, where the volume to mass ratio of the polar non-aqueous solvent to sufentanil base is from about 2:1 to about 12:1, and (b) contacting the mixture with citric acid to form a sufentanil citrate mixture, wherein the sufentanil citrate mixture is free of an oil phase.

Another aspect of this disclosure provides a process for forming sufentanil citrate from sufentanil base in the presence of water. The process comprises (a) forming a mixture of citric acid and water in which the volume to mass ratio of water to citric acid is from about 2:1 to about 12:1, and (b) adding sufentanil base to the mixture to form sufentanil citrate, wherein the mole to mole ratio of citric acid to sufentanil base is from about 2:1 to about 5.

A further aspect of this disclosure provides a process for forming sufentanil base from sufentanil citrate. The process comprises (a) contacting sufentanil citrate with at least one polar solvent to form a mixture, (b) contacting the mixture with a proton acceptor to form a sufentanil base mixture, (c) cooling the sufentanil base mixture to form solid sufentanil base, and (d) recovering the solid sufentanil base.

Other features and iterations of the invention are described in more detail below.

DETAILED DESCRIPTION OF THE INVENTION

Manufacturing sufentanil citrate is uniquely difficult compared to other sufentanil analogs in particular, as well as other active pharmaceuticals in general, because of sufentanil citrate's unusual and pronounced tendency to exit initially from the mother liquor as an oil prior to crystallization. The oily product initially coats the bottom and sides of the reaction vessel, agitator, and agitator shaft, and then solidifies as a glass within hours. The solidified product must then be manually removed, exposing the manufacturing operators to a hazardous potent compound for several hours every time this process is run. Scraping of the walls of a reactor is also undesirable. In the jargon of the development chemist, any process where an oil is formed or the product sticks to the reactor or other equipment is deemed "unscalable," because the process cannot be run using standard manufacturing operations and equipment—for example pumps, impellers, centrifuges, and filters—as opposed to a laboratory setting where material may be collected and moved by hand under visual observation.

Disclosed herein are processes for preparing sufentanil citrate which overcome the latter limitations; providing a scalable and robust process for producing sufentanil citrate without the need for intensive manual intervention. The present disclosure encompasses a process for forming sufentanil citrate from sufentanil base, and for recovering sufentanil base from the mother liquor. Applying the methods described herein, the crystallized sufentanil citrate product remains well-suspended in the mother liquor and does not aggregate, as is the problem with sufentanil citrate prepared with previous methods. The processes disclosed herein proceeds through a homogeneous solution phase, is reversible; compatible with a polishing filtration and with single step reprocessing. As a result, yield and process capabilities are improved.

(I) Process for Preparing Sufentanil Citrate from Sufentanil Base in a Polar Non-Aqueous Solvent One aspect of the disclosure encompasses a process for forming sufentanil citrate from sufentanil base in the presence of a polar non-aqueous solvent. The process comprises (a) contacting sufentanil base with a polar non-aqueous solvent to form a mixture, wherein the volume to mass ratio of the polar non-aqueous solvent to sufentanil base is from about 2:1 to about 12:1. The mixture is then (b) contacted with citric acid to form sufentanil citrate. In some embodiments, the process may further comprise (c) cooling the mixture from above to form solid sufentanil citrate, and (d) recovering solid sufentanil citrate.

As used herein, the term "mixture" refers to homogeneous (in solution) or heterogeneous (suspended) matrix. In some embodiments, the mixture may be a homogeneous or heterogeneous solution.

(a) Step A—Reaction Mixture

Step (a) of the process comprises contacting sufentanil base with a polar non-aqueous solvent to form a mixture. The process commences with the formation of a reaction mixture comprising sufentanil base and a polar non-aqueous solvent at a volume to mass ratio of the polar non-aqueous solvent to sufentanil base of from about 2:1 to about 12:1.

"Non-aqueous" solvent, as used herein, refers to solvents or solvent systems without an added water component but which are not necessarily "anhydrous" or "dry"; that is, trace amounts of water may accompany the solvent, for example, as water absorbed from the atmosphere or water derived from citric acid itself which can also exist as a monohydrate. The solvent may be a polar non-aqueous protic solvent or a polar non-aqueous aprotic solvent. Non-limiting examples of suitable polar non-aqueous protic solvents include alcohols such as methanol, ethanol, 1-propanol, 2-propanol, isobutanol, 1-butanol, 2-butanol, sec-butanol, t-butanol, and the like; diols such as propylene glycol; amides such as formamide, acetamide, and the like; and combinations of any of the above. Non-limiting examples of suitable polar non-aqueous aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran (THF), trichloromethane, and combinations thereof. Specific polar non-aqueous solvents that may be employed include, for example, ethyl acetate, isopropyl acetate, methyl isobutyl ketone, methyl ethyl ketone, and $C_1$-$C_5$ alcohol, such as methanol, ethanol, 1-propanol, 2-propanol (isopropyl alcohol, IPA), 1-butanol, 2-butanol, sec-butanol, and tert-butanol, and combinations thereof.

In particular embodiments, the polar non-aqueous solvent may be a U.S. Food and Drug Administration (FDA) Class 3 approved solvent. The FDA defines Class 3 solvents as including no solvent known as a human health hazard at levels normally accepted in pharmaceuticals. Available data indicate that Class 3 solvents are less toxic than other solvents in acute or short-term studies and are negative in genotoxicity studies. The FDA considers amounts of these residual solvents of 50 mg per day or less (corresponding to 5,000 ppm or 0.5 percent) as acceptable without justification. Higher amounts may also be acceptable provided they are realistic in relation to manufacturing capability and good manufacturing practice (GMP). Examples of suitable polar non-aqueous FDA Class 3 solvents include, but are not limited to, acetic acid, acetone, anisole, 2-butanol, butyl acetate, tert-butylmethyl ether, DMSO, ethanol, ethyl acetate, ethyl ether, ethyl formate, formic acid, isobutyl acetate, isopropyl acetate, methyl acetate, 3-methyl-1-butanol, methylethyl ketone (MEK), methylisobutyl ketone (MIBK), 2-methyl-1-propanol, 1-pentanol, 1-propanol, 2-propanol, propyl acetate, and tetrahydrofuran (THF). In exemplary embodiments, the solvent may be ethyl acetate, isopropyl acetate, MEK, MIBK, 1-butanol, 2-butanol, ethanol, 1-propanol, 2-propanol (isopropyl alcohol, IPA), or 2-methyl-1-propanol (isobutanol).

In general, the volume to mass ratio of the solvent to sufentanil base ranges from about 2:1 to about 12:1. In various embodiments, the volume to mass ratio of the solvent to sufentanil base may range from about 2:1 to about 12:1, from about 2.5:1 to about 10:1, from about 3:1 to about 8:1, or from about 3.5:1 to about 6:1. In exemplary embodiments, the volume to mass ratio of the solvent to sufentanil base may be from about 4:1 to about 5:1.

(b) Step A—Reaction Conditions

In general, contact between the polar non-aqueous solvent and sufentanil base is conducted at a temperature that ranges from about 20° C. to about 90° C. In various embodiments, the reaction may be conducted at a temperature from about 20° C. to about 30° C., from about 30° C. to about 40° C., from about 40° C. to about 50° C., from about 50° C. to about 60° C., from about 60° C. to about 70° C., from about 70° C. to about 80° C., or from about 80° C. to about 90° C. In exemplary embodiments, the reaction may be conducted at a temperature of about 50° C. In other exemplary embodiments, the contacting may be conducted at a temperature from about 60° C. to about 80° C., for example at about 70° C. The contacting may be conducted in an inert atmosphere (e.g., under nitrogen or argon) and under ambient pressure. Contact between the polar non-aqueous solvent and sufentanil base may be facilitated by stirring, mixing, shaking, or any other means known in the art.

Typically, the contacting step is allowed to proceed for a sufficient period of time until the sufentanil base is incorporated into the mixture. In some embodiments, the mixture may be a homogenous solution. Generally, the contacting may proceed from about 1 minute to about 60 minutes. In some embodiments, the reaction may proceed from about 1 minute to about 5 minutes, from about 5 minutes to about 10 minutes, from about 10 minutes to about 15 minutes, from about 15 minutes to about 20 minutes, from about 20 minutes to about 25 minutes, from about 25 minutes to about 30 minutes, from about 30 minutes to about 35 minutes, from about 35 minutes to about 40 minutes, from about 40 minutes to about 45 minutes, from about 45 minutes to about 50 minutes, from about 50 minutes to about 55 minutes, or from about 55 minutes to about 60 minutes.

In some embodiments, the mixture may be filtered (polishing filtration) before proceeding to the next step. In particular, the mixture may be filtered at a temperature that ranges from about 20° C. to about 90° C., as described above, in order to remove, for example, undissolved sufentanil base or other impurities before proceeding to reaction with citric acid.

(c) Step B—Reaction Mixture

Step (b) of the process further comprises contacting the mixture from step (a) with citric acid to form sufentanil citrate. The process commences with the formation of a reaction mixture comprising the mixture from step (a), which is detailed above, and citric acid, which may be added directly to the mixture from step (a) as a solid or a solution in a solvent.

The reaction mixture comprises citric acid. The citric acid may be present as the anhydrate, where the crystalline structure of the citric acid is not associated with any water molecules, or a hydrate, where the crystalline structure of the citric acid is associated with one or more water molecules. Examples of suitable hydrates include citric acid hemihydrate, citric acid monohydrate, citric acid sesquihydrate, citric acid dihydrate, and citric acid trihydrate.

In some embodiments, the citric acid may be dissolved in a solvent, as defined above in section (I)(a) above. In exemplary embodiments, the solvent may be ethyl acetate, isopropyl acetate, methyl isobutyl ketone, methyl ethyl ketone, or $C_1$-$C_5$ alcohol. In general, the volume to mass ratio of the solvent to the citric acid ranges from about 0.1:1 to about 10:1. In various embodiments, the volume to mass ratio of the solvent to citric acid may range from about 0.1:1 to about 10:1, from about 0.2:1 to about 8:1, from about 0.3:1 to about 6:1, from about 0.4:1 to about 4:1, or from about 0.5:1 to about 2:1. In exemplary embodiments, the volume to mass ratio of the solvent to citric acid may be from about 0.5:1 to about 2:1, or about 1:1.

The amount of citric acid added to the reaction mixture can and will vary. In general, the mole to mole ratio of citric acid to sufentanil base may range from about 0.9:1 to about 1.5:1. In various embodiments, the mole to mole ratio of citric acid to sufentanil base may range from about 0.9:1 to about 1.5:1, from about 0.92:1 to about 1.4:1, from about 0.94:1 to about 1.3:1, from about 0.96:1 to about 1.2:1, or from about 0.98:1 to about 1.1:1. In exemplary embodiments, the mole to mole ratio of citric acid to sufentanil base may range from about 0.9:1 to about 1.1:1.

(d) Step B—Reaction Conditions

The temperature at which contact between citric acid and the mixture of (a) is conducted can and will vary. In general, the contacting is conducted at a temperature that ranges from about 20° C. to about 90° C. In various embodiments, the contacting may be conducted at a temperature from about 20° C. to about 30° C., from about 30° C. to about 40° C., from about 40° C. to about 50° C., from about 50° C. to about 60° C., from about 60° C. to about 70° C., from about 70° C. to about 80° C., or from about 80° C. to about 90° C. In an exemplary embodiment, the contacting may be conducted at a temperature of about 80° C. In other exemplary embodiments, the contacting may be conducted at a temperature from about 60° C. to about 75° C., for example at about 70° C. The contacting may be conducted in an inert atmosphere (e.g., under nitrogen or argon) and under ambient pressure. Contact between citric acid and sufentanil base in the mixture of (a) may be facilitated by stirring, mixing, shaking, or any other means known in the art. In various embodiments, the mixture of step (b) may be substantially or completely free of an oil phase comprising a sufentanil species. In particular, in embodiments in which the polar non-aqueous solvent is 2-propanol, the mixture of (b) is devoid of an oil phase.

Typically, the reaction is allowed to proceed for a sufficient period of time until the reaction is complete, as determined by any of numerous methods known in the art. In this context, a "completed reaction" generally means that the reaction mixture contains a significantly diminished amount of sufentanil base, and a significantly increased amount of sufentanil citrate compared to the amounts of each present at the beginning of the reaction. In a completed reaction, the amount of sufentanil base remaining in the reaction mixture may be less than about 3%, or less than about 1%. In general, the reaction may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

In embodiments where the citric acid is dissolved in solvent before addition to the mixture of step (a), the citric acid solution may be added over a period of about 1 minute to about 60 minutes. In some embodiments, the citric acid solution may be added over a period of about 1 minute to about 5 minutes, of about 5 minutes to about 10 minutes, of about 10 minutes to about 15 minutes, of about 15 minutes to about 20 minutes, of about 20 minutes to about 25 minutes, of about 25 minutes to about 30 minutes, of about 30 minutes to about 35 minutes, of about 35 minutes to about 40 minutes, of about 40 minutes to about 45 minutes, of about 45 minutes to about 50 minutes, of about 50 minutes to about 55 minutes, or of about 55 minutes to about 60 minutes. In a particular embodiment, the citric acid solution may be added over a period of about 50 minutes.

In some embodiments, the mixture may be filtered (polishing filtration) before proceeding to the next step. In particular, the mixture may be filtered at a temperature that ranges from about 20° C. to about 90° C., as described above.

The sufentanil citrate in the mixture may be isolated from the mixture using techniques known to those of skill in the art. Non-limiting examples of suitable techniques include precipitation, extraction, evaporation, distillation, chromatography, and crystallization. In exemplary embodiments, the sufentanil citrate may be isolated according to the methods described in the sections (I)(e)-(f) below. The sufentanil citrate may be used as is, or may be converted to another compound using techniques familiar to those of skill in the art.

The yield of sufentanil citrate can and will vary. Typically, the yield of sufentanil citrate may be at least about 35%. In one embodiment, the yield of sufentanil citrate may range from about 35% to about 65%. In another embodiment, the yield of sufentanil citrate may range from about 65% to about 75%. In yet another embodiment, the yield of sufentanil citrate may range from about 75% to about 85%. In a further embodiment, the yield of the sufentanil citrate may range from about 85% to about 95%. In still another embodiment, the yield of the sufentanil citrate may be greater than about 95%. In still a further embodiment, the yield of the sufentanil citrate may be greater than about 99%.

(e) Step C

In some embodiments, the process may further comprise step (c) which comprises cooling the mixture from step (b) to form solid sufentanil citrate. Generally, the reaction mixture of step (c) is the same as the reaction mixture of step (b), but in some embodiments, the reaction mixture of step (b) may be seeded with crystals of sufentanil citrate. For example, in embodiments in which the polar non-aqueous solvent is 2-propanol, seed crystals of sufentanil citrate may be added to the mixture of step (b). In general, the mole to mole ratio of sufentanil citrate seed crystals to sufentanil citrate in the mixture may range from about 0.0001:1 to about 0.05:1. In various embodiments, the mole to mole ratio of sufentanil citrate seed crystals to sufentanil citrate in the mixture may range from about 0.0001:1 to about 0.0005:1, from about 0.0005:1 to about 0.001:1, from about 0.001:1 to about 0.005:1, from about 0.005:1 to about 0.01:1, or from about 0.01:1 to about 0.05:1. In an exemplary embodiment, the mole to mole ratio of sufentanil citrate seed crystals to sufentanil citrate in the mixture may range from about 0.001:1 to about 0.05:1.

The temperature to which the reaction mixture of step (b) may be seeded can and will vary. In general, the temperature will range from 30° C. to about 70° C. In various embodiments, the temperature may range from about 30° C. to about −40° C., from about 40° C. to about 50° C., from about 50° C. to about 60° C., or from about 60° C. to about 70° C. In preferred embodiments, the temperature range in which the reaction may be seeded may be about 60° C.

The temperature to which the mixture of (b) is cooled can and will vary. In general, the temperature will range from about −20° C. to about 70° C. In various embodiments, the temperature may range from about −20° C. to about −10° C., from about −10° C. to about 0° C., from about 0° C. to about 5° C., from about 5° C. to about 10° C., from about 10° C. to about 20° C., from about 20° C. to about 30° C., from about 30° C. to about 40° C., from about 40° C. to about 50° C., from about 50° C. to about 60° C., or from about 60° C. to about 70° C. In some embodiments, the temperature of the reaction is cooled may range from about −5° C. to about 5° C. In a preferred embodiment, the temperature of the cooled reaction may be about 50° C.

Typically, the reaction is allowed to proceed for a sufficient period of time until the reaction is complete, as detailed above. For example, the cooling step may proceed until no further (visibly detectable or by laser methods) solid sufentanil citrate is formed. In general, the reaction may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

(f) Step D

In some embodiments, the process may further comprise step (d) which comprises recovering the solid sufentanil citrate from the mixture of step (c). In particular, the solid sufentanil citrate may be recovered from the mixture of step (c) through filtration, for example through vacuum filtration. The temperature at which the recovering step is conducted can and will vary. In general, the temperature will range from about −20° C. to about 60° C. In various embodiments, the temperature may range from about −20° C. to about −10° C., from about −10° C. to about 0° C., from about 0° C. to about 5° C., from about 5° C. to about 10° C., from about 10° C. to about 20° C., from about 20° C. to about 30° C., from about 30° C. to about 40° C., from about 40° C. to about 50° C., or from about 50° C. to about 60° C. In an exemplary embodiment, the temperature of the recovering step may be about 50° C.

The yield of solid sufentanil citrate can and will vary. Typically, the yield of solid sufentanil citrate may be at least about 35%. In one embodiment, the yield of solid sufentanil citrate may range from about 35% to about 65%. In another embodiment, the yield of solid sufentanil citrate may range from about 65% to about 75%. In yet another embodiment, the yield of solid sufentanil citrate may range from about 75% to about 85%. In a further embodiment, the yield of the solid sufentanil citrate may range from about 85% to about 95%. In still another embodiment, the yield of the solid sufentanil citrate may be greater than about 95%. In further embodiments, the yield of sufentanil citrate may be greater than about 99%. In an exemplary embodiment, the solid sufentanil citrate recovered at step (d) may have a yield of at least about 85%.

The solid sufentanil citrate also may be further dried using any method known in the art to remove residual solvent. Suitable methods include vacuum filtration, oven drying, and reduction in vacuo, for example on a rotary evaporator or attached to a high vacuum manifold. In further embodiments, the solid sufentanil citrate may be dried at elevated temperature, for example from about 35° C. to about 65° C.

In various embodiments, the solid sufentanil citrate recovered at step (d) may contain less than about 5000 ppm of solvent, for example, less than about 4500 ppm, less than about 4000 ppm, less than about 3500 ppm, less than about 3000 ppm, less than about 2500 ppm, less than about 2000 ppm, less than about 1500 ppm, less than about 1000 ppm, less than about 500 ppm, or less than about 100 ppm. In other embodiments, the solid sufentanil citrate recovered at step (d) may contain more than about 5000 ppm of solvent. In a preferred embodiment, the solid sufentanil citrate recovered in step (d) may contain less than 2000 ppm of solvent.

(g) Further processing

The mixture remaining from step (d) after the recovery of solid sufentanil citrate may be further processed according to section (III) below to provide recoverable solid sufentanil base.

(II) Processes for Preparing Sufentanil Citrate from Sufentanil Base in Water

Another aspect of the present disclosure provides processes for forming sufentanil citrate from sufentanil base in the presence of water. In general, the processes comprise (a) forming a mixture of citric acid and water and (b) adding sufentanil base to the mixture to form sufentanil citrate. The processes for forming sufentanil citrate in presence of water can be divided into two iterations of the general process.

The first water method comprises forming a mixture with a high concentration of citric acid during the first step of the process (a1), wherein the volume to mass ratio of water to citric acid is from about 2:1 to about 12:1, and adding sufentanil base during the second step of the process (b1), wherein the mole to mole ratio of citric acid to sufentanil base in the mixture of (a1) ranges from about 2:1 to about 5:1; and step (b1) generally is performed at a temperature of 85° C. or less. In some instances, this iteration may further comprise (c1) cooling the mixture from step (b1) to form solid sufentanil citrate, and (d1) recovering solid sufentanil citrate.

The second water method comprises forming two different mixtures of sufentanil citrate, wherein one mixture is added to the other mixture. The first (high citric acid) mixture of sufentanil citrate is prepared by (a2) forming a first mixture of citric acid and water in which the volume to mass ratio of water to citric acid is from about 2:1 to about 12:1; and (b2) adding about 4% to about 35% of the total amount of sufentanil base to the first mixture of citric acid and water, wherein mole to mole ratio of citric acid to sufentanil base ranges from about 2:1 to about 5:1. The method further comprises (c2) cooling the first mixture of sufentanil citrate. A second (low citric acid) mixture of sufentanil citrate is prepared by (d2) forming a second mixture of citric acid and water in which the volume to mass ratio of water to citric acid is from about 10:1 to about 22:1, and (e2) adding about 65% to about 96% of the total amount of sufentanil base to the second mixture of citric acid and water, wherein the mole to mole ratio of citric acid to sufentanil base ranges from about 0.5:1 to about 2:1. The method further comprises (f2) adding the second (low citric acid) mixture of sufentanil citrate from step (e2) to the first (high citric acid) mixture of sufentanil citrate from step (c2); and (g2) cooling the mixture from step (f2) to form solid sufentanil citrate. This method may further comprise (h2) recovering the solid sufentanil citrate.

Each of these methods is presented in more detail below:

(a) Water Method 1

(i) Step A1

In the first iteration of the process for preparing sufentanil citrate from sufentanil base in the presence of water, step (a1) comprises forming a mixture of citric acid and water.

The citric acid may be present in any form described above in section (I)(c). In general, the volume to mass ratio of water to citric acid may range from about 2:1 to about 12:1. In various embodiments, the volume to mass ratio of water to citric acid may range from about 2:1 to about 12:1, from about 3:1 to about 11:1, from about 4:1 to about 10:1, from about 5:1 to about 9:1, or from about 6:1 to about 8:1, or from about 6.5:1 to about 7.5:1. In some embodiments, the volume to mass ratio of water to citric acid may be about 7:1.

The reaction between citric acid and water is conducted at a temperature of about 100° C. or less. For example, the temperature may range from about 20° C. to about 40° C., from about 40° C. to about 60° C., from about 60° C. to about 80° C., or from about 80° C. to about 100° C. In exemplary embodiments, the temperature may range from about 20° C. to about 30° C.

In general, citric acid is added in one portion. The contacting step is allowed to proceed for a sufficient period of time until the citric acid is incorporated into the mixture. In some embodiments, the mixture may be a homogenous solution. Generally, the contacting may proceed from about 1 minute to about 60 minutes. In some embodiments, the reaction may proceed from about 1 minute to about 5 minutes, from about 5 minutes to about 10 minutes, from about 10 minutes to about 15 minutes, from about 15 minutes to about 20 minutes, from about 20 minutes to about 25 minutes, from about 25 minutes to about 30 minutes, from about 30 minutes to about 35 minutes, from about 35 minutes to about 40 minutes, from about 40 minutes to about 45 minutes, from about 45 minutes to about 50 minutes, from about 50 minutes to about 55 minutes, or from about 55 minutes to about 60 minutes. Contact between citric acid and water may be facilitated by stirring, mixing, shaking, or any other means known in the art.

The reaction may be conducted in an inert atmosphere (e.g., under nitrogen or argon) and under ambient pressure. In various embodiments, the mixture of (a1) may be substantially or completely free of undissolved species. In some embodiments, the mixture of (a1) may be filtered (polishing filtration) to remove undissolved impurities before proceeding to the next step.

(ii) Step B1

Step (b1) of this iteration comprises adding sufentanil base to the mixture of (a1).

In general, the mole to mole ratio of citric acid to sufentanil base may range from about 2:1 to about 5:1. In various embodiments, the mole ratio of citric acid to sufentanil base may range from about 2.0:1 to 5.0:1, from about 2.25:1 to 4.5:1, from about 2.5:1 to about 4.0:1, or from about 2.75:1 to about 3.5:1. In exemplary embodiments, the mole to mole ratio of citric acid to sufentanil base may range from about 2.0:1 to about 3.0:1.

The reaction between the sufentanil base and citric acid mixture generally is conducted at a temperature of about 85° C. or less. For example, the temperature may range from about 20° C. to about 40° C., from about 40° C. to about 60° C., from about 60° C. to about 70° C., or from about 70° C. to about 85° C. In exemplary embodiments, the temperature may range from about 60° C. to about 85° C.

In general, sufentanil base is added on one portion. Contact between sufentanil base and citric acid may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours. Contact between sufentanil base and citric acid may be facilitated by stirring, mixing, shaking, or any other means known in the art.

The reaction may be conducted in an inert atmosphere (e.g., under nitrogen or argon) and under ambient pressure. In various embodiments, the mixture of (b1) may be substantially or completely free of an oil phase comprising a sufentanil species. In some embodiments, the mixture of (b1) may be filtered to remove undissolved sufentanil base and/or other impurities before proceeding to the next step.

(iii) Step C1

In various instances, this iteration may further comprise (c1) cooling the mixture from step (b1) to form solid sufentanil citrate, and (d1) recovering solid sufentanil citrate from the mixture of (c1).

In some instances, this iteration may further comprise (c1) cooling the mixture from step (b1) to form solid sufentanil citrate. The temperature to which the mixture of (b1) is cooled can and will vary. In general, the temperature may range from about −20° C. to about 60° C. In various embodiments, the temperature may range from about 20° C. to about −10° C., from about −10° C. to about 0° C., from about 0° C. to about 5° C., from about 5° C. to about 10° C., from about 10° C. to about 20° C., from about 20° C. to about 30° C., from about 30° C. to about 40° C., from about 40° C. to about 50° C., or from about 50° C. to about 60° C. In some embodiments, the temperature of the reaction may range from about 0° C. to about 5° C. In other embodiments, the temperature of the reaction may be less than about −5° C.

Typically, the reaction is allowed to proceed for a sufficient period of time until the reaction is complete. For example, the cooling step may proceed until no further (visibly detectable or by lasers) solid sufentanil citrate is formed. In general, the reaction may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

(iv) Step D1

This iteration also may further comprise (d1) recovering the solid sufentanil citrate after step (c1). The solid sufentanil citrate may be recovered from the mixture of step (c1) through filtration, for example through vacuum filtration. The temperature at which the recovering step is conducted can and will vary. In general, the temperature may range from about −20° C. to about 60° C. In various embodiments, the temperature may range from about −20° C. to about −10° C., from about −10° C. to about 0° C., from about 0° C. to about 5° C., from about 5° C. to about 10° C., from about 10° C. to about 20° C., from about 20° C. to about 30° C., from about 30° C. to about 40° C., from about 40° C. to about 50° C., or from about 50° C. to about 60° C. In exemplary embodiments, the temperature of the recovering step may range from about 0° C. to about 25° C.

The yield of solid sufentanil citrate can and will vary. Typically, the yield of solid sufentanil citrate may be at least about 35%. In one embodiment, the yield of solid sufentanil citrate may range from about 35% to about 65%. In another embodiment, the yield of solid sufentanil citrate may range from about 65% to about 75%. In yet another embodiment, the yield of solid sufentanil citrate may range from about 75% to about 85%. In a further embodiment, the yield of the solid sufentanil citrate may range from about 85% to about 95%. In still another embodiment, the yield of the solid sufentanil citrate may be greater than about 95%. In further embodiments, the yield of sufentanil citrate may be greater than about 99%. In an exemplary embodiment, the solid sufentanil citrate recovered at step (d1) may have a yield of at least about 90%.

The solid sufentanil citrate also may be further dried using any method known in the art to remove water. Suitable methods include vacuum filtration, oven drying, and reduction in vacuo, for example on a rotary evaporator or attached to a high vacuum manifold. In further embodiments, the solid sufentanil citrate may be dried at elevated temperature, for example from about 35° C. to about 65° C.

The mixture remaining after the recovery of solid sufentanil citrate at step (d1) may be further processed according to section (III) below to provide solid sufentanil base.

(b) Water Method 2

The second iteration of the process for preparing sufentanil citrate from sufentanil base in the presence of water comprises forming two different mixtures of sufentanil citrate and then combining the two mixtures.

(i) Step A2

The first step of this iteration comprises forming a first mixture of citric acid and water, in which the concentration of citric acid is high. Forming the mixture of citric acid and water is essentially identical to that described above in section (II)(a)(i).

In general, the volume to mass ratio of water to citric acid in the high citric acid mixture may range from about 2:1 to about 12:1. In various embodiments, the volume to mass ratio of water to citric acid in the high citric acid mixture may range from about 1:1 to about 9:1, from about 2:1 to about 8:1, from about 3:1 to about 7:1, or from about 4:1 to about 6:1. In some embodiments, the volume to mass ratio of water to citric acid in the high citric acid mixture may be about 5:1.

(ii) Step B2

The next step of this iteration comprises forming the first mixture of sufentanil citrate (high citric acid) by adding about 4% to about 35% of the total amount of sufentanil base to the high citric acid mixture of (a2). In general, the mole to mole ratio of citric acid to sufentanil base may range from about 2:1 to about 5:1. In various embodiments, the mole ratio of citric acid to sufentanil base may range from about 2.0:1 to 5.0:1, from about 2.25:1 to 4.5:1, from about 2.5:1 to about 4.0:1, or from about 2.75:1 to about 3.5:1. In exemplary embodiments, the mole to mole ratio of citric acid to sufentanil base may range from about 2.0:1 to about 3.0:1. In various embodiments, the amount of sufentanil base added to the first mixture of aqueous citric acid may range from about 4% to about 10%, from about 10% to about 15%, from about 15% to about 20%, from about 20% to about 25%, from about 25% to about 30%, or from about 30% to about 35% total amount of sufentanil base. In exemplary embodiments, the amount of sufentanil base added to the first mixture of (a2) may be 10% to about 20%, or about 15%, of the total amount of sufentanil base.

In general, step (b2) of the process is conducted at a temperature of 90° C. or less. In various embodiments, the reaction may be conducted at a temperature from about 20° C. to about 40° C., from about 40° C. to about 60° C., from about 60° C. to about 80° C., or from about 80° C. to about 90° C. In exemplary embodiments, the temperature may range from about 70° C. to about 85° C.

Contact between sufentanil base and the high citric acid mixture at step (b2) may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours. Contact between sufentanil base and high citric acid mixture may be facilitated by stirring, mixing, shaking, or any other means known in the art.

The reaction may be conducted in an inert atmosphere (e.g., under nitrogen or argon) and under ambient pressure. In various embodiments, the mixture of (b2) may be substantially or completely free of an oil phase comprising a sufentanil species. In some embodiments, the mixture of (b2) may be filtered (polishing filtration) to remove undissolved sufentanil base and/or other impurities before proceeding to the next step.

(iii) Step C2

The third step of this iteration comprises cooling the first sufentanil citrate mixture (high citric acid) of (b2). The cooling step may be conducted essentially as described above in section (II)(a)(iii).

(iv) Step D2

Step (d2) comprises forming a second mixture of citric acid and water, in which the concentration of citric acid is lower than the previous charge (a2).

In general, the volume to mass ratio of water to citric acid in the low citric acid mixture may range from about 10:1 to about 22:1. In various embodiments, the volume to mass ratio of water to citric acid in the low citric acid mixture may range from about 10:1 to about 22:1, from about 12:1 to about 20:1, or from about 14:1 to about 18:1. In some embodiments, the volume to mass ratio of water to citric acid may be about 16.5:1. The second mixture of citric acid and water may be formed essentially as described above in section (II)(a)(i).

(v) Step E2

The next step of this iteration comprises forming a second mixture of sufentanil citrate (low citric acid) by adding about 65% to about 96% of the total amount of sufentanil base to the low citric acid mixture of (d2). In general, the mole to mole ratio of citric acid to sufentanil base may range from about 0.5:1 to about 3.0:1. In various embodiments, the mole ratio of citric acid to sufentanil base may range from about 0.5:1 to 3.0:1, from about 0.75:1 to 2.0:1, or from about 0.9:1 to about 1.1:1. In exemplary embodiments, the mole to mole ratio of citric acid to sufentanil base may be about 1.0:1. In various embodiments, the amount of sufentanil base added to the mixture of (d2) may be range from about 65% to about 70%, from about 70% to about 75%, from about 75% to about 80%, from about 80% to about 85%, from about 85% to about 90%, from about 90% to about 96% of total amount of sufentanil base used in the process. In exemplary embodiments, the amount of sufentanil bases added to the mixture of (d2) may range from about 80% to about 90%, or about 85%, of the total amount of sufentanil base.

In general, step (e2) is conducted at a temperature of at least about 90° C. For example, the step may be conducted at a temperature ranging from about 90° C. to about 95° C., from about 95° C. to about 100° C., or greater than about 100° C.

Contact between sufentanil base and the low citric acid mixture at step (e2) may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours. Contact between sufentanil base and citric acid may be facilitated by stirring, mixing, shaking, or any other means known in the art.

The reaction may be conducted in an inert atmosphere (e.g., under nitrogen or argon) and under ambient pressure. In various embodiments, the mixture of (e2) may be substantially or completely free of an oil phase comprising a sufentanil species. In some embodiments, the mixture of (e2) may be filtered (polishing filtration) to remove undissolved sufentanil base and/or other impurities before proceeding to the next step.

(vi) Step F2

The second iteration further comprises (f2) adding the (hot) second mixture of sufentanil citrate (low citric acid) from step (e2) to the first mixture of sufentanil citrate (high citric acid) from step (c2). In general, the first mixture of sufentanil citrate is kept at a temperature that ranges from about 5° C. to about 30° C. while the second mixture is added to the first mixture. In some embodiments, the temperature of the first mixture may range from about 5° C. to about 10° C., from about 10 to about 20° C., or from about 20 ° C. to about 30° C. In exemplary embodiment, the temperature of the first mixture is kept at about 10° C. to about 23° C. during addition of the second mixture.

The addition of the second mixture to the first mixture may occur over a period of about 0.5 hour to about 4 hours. In various embodiments, the duration of the addition may range from about 0.5 to about 1 hour, from about 1 hour to about 2 hours, or from about 2 hours to about 3 hours. In exemplary embodiments, the duration of the addition may be about two hours. The first mixture may be stirred or mixed during the addition of the second mixture.

(vii) Step G2

The next step of the iteration comprises cooling the mixture of (f2) to form solid sufentanil citrate. The cooling step may be conducted essentially as described above in section (II)(a)(iii).

(viii) Step H2

This iteration may further comprise (h2) recovering the solid sufentanil citrate from the mixture of (g2), essentially as detailed above in section (II)(a)(iv). The mixture remaining after the recovery of the solid sufentanil citrate at step (h2) may be further processed according to section (III) below to provide solid sufentanil base.

(III) Process for Forming Sufentanil Base from Sufentanil Citrate in Solvent

Another aspect of the present disclosure provides a process for forming sufentanil base from sufentanil citrate. The process comprises (a) contacting sufentanil citrate with at least one polar solvent to form a mixture; and (b) contacting the mixture with a proton acceptor (a base), thereby forming sufentanil base. The process may further comprise (c) optionally cooling the mixture from step (b) to form solid sufentanil base; and (d) recovering solid sufentanil base.

In various embodiments, step (a) of the process for forming sufentanil base from sufentanil citrate is omitted and the process is conducted using a mixture remaining after recovery of solid sufentanil citrate during any of the processes detailed in sections (I) or (II) above. In particular, refer to sections (I)(g), (II)(a)(iv), and (II)(b)(viii).

(a) Step A—Reaction Mixture

Step (a) of the process comprises contacting sufentanil citrate with at least one polar solvent to form a mixture. The process commences with the formation of a mixture comprising sufentanil citrate and at least one polar solvent. The at least one polar solvent may be any polar non-aqueous solvent described above at section (I)(a), water, or combinations thereof. In various embodiments, the at least one polar solvent may be selected from the group consisting of ethyl acetate, isopropyl acetate, methyl isobutyl ketone, methyl ethyl ketone, $C_1$-$C_5$ alcohol, or water. In some exemplary embodiments, the at least one polar solvent may be 2-propanol. In other exemplary embodiments, the at least one polar solvent may be water. In still other exemplary embodiments, the polar solvent comprises ethanol and water.

In general, the volume to mass ratio of the solvent to sufentanil citrate ranges from about 0.5:1 to about 200:1. In various embodiments, the volume to mass ratio of the solvent to sufentanil citrate may range from about 0.5:1 to 200:1, from about 1.25:1 to 150:1, from about 2.5:1 to 100:1, or from about 3.75:1 to about 50:1. In exemplary embodiments, the volume to mass ratio of the solvent to sufentanil citrate may range from about 5:1 to about 25:1.

(b) Step A—Reaction Condtiions

In general, contact between the polar solvent and sufentanil citrate is conducted at a temperature that ranges from about 20° C. to about 90° C. In various embodiments, the temperature may range from about 20° C. to about 30° C., from about 30° C. to about 40° C., from about 40° C. to about 50° C., from about 50° C. to about 60° C., from about 60° C. to about 70° C., from about 70° C. to about 80° C., or from about 80° C. to about 90° C. Typically, contact between the polar solvent and sufentanil citrate is allowed to proceed for a sufficient period of time until a homogenous mixture forms. The duration of contact may range from about several minutes to several hours.

In some embodiments, the mixture may be filtered (polishing filtration) before proceeding to the next step. In particular, the mixture may be filtered at a temperature that ranges from about 20° C. to about 90° C., as described above, in order to remove, for example, undissolved sufentanil citrate or other impurities before proceeding to reaction with a proton acceptor.

(c) Step B—Reaction Mixture

Step (b) of the process further comprises contacting the mixture from step (a) with a proton acceptor, thereby forming sufentanil base. In general, the pKa of suitable proton acceptors ranges from about 7 to about 13. The proton acceptor may be organic or inorganic. Representative inorganic salts include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), and combinations of any of the foregoing. In exemplary embodiments, the proton acceptor comprises a hydroxide. In particular embodiments, the proton acceptor may be potassium hydroxide, sodium hydroxide, or combinations thereof.

The mole to mole ratio of sufentanil citrate to the proton acceptor may range from about 1:1.0 to about 1:6.0. In some embodiments, the mole to mole ratio of sufentanil citrate to the proton acceptor may range from about 1:1.0 to 1:6.0, from about 1:1.1 to about 1:5.0, from about 1:1.3 to 1:4.0, or from about 1:1.5 to about 1:3.0. In some embodiments, the mole to mole ratio of sufentanil citrate to the proton acceptor may be from about 1:1.6 to about 1:2.0.

(d) Step B—Reaction Conditions

The temperature at which the reaction is conducted can and will vary. In general, the reaction is conducted at a temperature that ranges from about 20° C. to about 90° C. In various embodiments, the reaction may be conducted at a temperature from about 20° C. to about 30° C., from about 30° C. to about 40° C., from about 40° C. to about 50° C., from about 50° C. to about 60° C., from about 60° C. to about 70° C., from about 70° C. to about 80° C., or from about 80° C. to about 90° C. In exemplary embodiments, the reaction is conducted at a temperature of about 35° C. The reaction may be conducted in an inert atmosphere (e.g., under nitrogen or argon) and under ambient pressure.

Typically, the reaction is allowed to proceed for a sufficient period of time until the reaction is complete. In a completed reaction, the amount of sufentanil citrate remaining in the reaction mixture may be less than about 3%, or less than about 1%. In general, the reaction may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

The sufentanil base may be isolated from the reaction mixture using techniques known to those of skill in the art. Non-limiting examples of suitable techniques include precipitation, extraction, evaporation, distillation, chromatography, and crystallization. In exemplary embodiments, the sufentanil base may be isolated according to the methods described in the sections (III)(e)-(f) below. The sufentanil base may be used as is, or may be converted to another compound using techniques familiar to those of skill in the art.

The yield of sufentanil base can and will vary. Typically, the yield of sufentanil base may be at least about 35%. In one embodiment, the yield of sufentanil base may range from about 35% to about 65%. In another embodiment, the yield of sufentanil base may range from about 65% to about 75%. In yet another embodiment, the yield of sufentanil base may range from about 75% to about 85%. In a further embodiment, the yield of the sufentanil base may range from about 85% to about 95%. In still another embodiment, the yield of the sufentanil base may be greater than about 95%.

(e) Step C

In some embodiments, step (c) of the process may further comprise cooling the mixture from step (b) to form solid sufentanil base. Generally, the reaction mixture of step (c) is the same as the reaction mixture of step (b), but in some embodiments, the reaction mixture of step (b) may be seeded with crystals of sufentanil base. In general, the mole to mole ratio of sufentanil base seed crystals to sufentanil base in the mixture may range from about 0.0001:1 to about 0.05:1. In various embodiments, the mole to mole ratio of sufentanil base seed crystals to sufentanil base in the mixture may range from about 0.0001:1 to 0.05:1, from about 0.00025:1 to 0.05:1, from about 0.0005:1 to 0.05:1, or from about 0.00075:1 to 0.05:1. In an exemplary embodiment, the mole to mole ratio of sufentanil base seed crystals to sufentanil base in the mixture may range from about 0.001:1 to about 0.05:1.

The temperature to which the mixture is cooled can and will vary. In general, the temperature may range from about −20° C. to about 60° C. In various embodiments, the temperature may range from about −20° C. to about −10° C., from about −10° C. to about 0° C., from about 0° C. to about 5° C., from about 5° C. to about 10° C., from about 10° C. to about 20° C., from about 20° C. to about 30° C., from about 30° C. to about 40° C., from about 40° C. to about 50° C., or from about 50° C. to about 60° C. In exemplary embodiments, the temperature may range from about 0° C. to about 5° C.

Typically, step (c) is allowed to proceed for a sufficient period of time until the reaction is complete, as detailed above. For example, the cooling step may proceed until no further (visible detectable) solid sufentanil base is formed. In general, the reaction may proceed for about 0.5 hours to about 24 hours. In some embodiments, the reaction may proceed from about 0.5 hours to about 1 hour, from about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours.

(f) Step D

In some embodiments, the process further comprises step (d) which comprises recovering solid sufentanil base from the mixture of step (c). In particular, the solid sufentanil base may be recovered from the reaction mixture of step (c) through filtration, for example through vacuum filtration. The solid sufentanil base may then be further dried using any method known in the art to remove residual solvent. Suitable methods include vacuum filtration, oven drying, and reduction in vacuo, for example on a rotary evaporator or attached to a high vacuum manifold. In further embodiments, the solid sufentanil base may be dried at elevated temperature, for example from about 35° C. to about 65° C.

In some embodiments, the solid sufentanil base may be contacted with a non-polar solvent to form crystalline sufentanil base. Representative nonpolar solvents include, but are not limited to, alkane and substituted alkane solvents (including cycloalkanes), aromatic hydrocarbons, and combinations thereof. Specific nonpolar solvents that may be employed include, for example, benzene, chlorobenzene, chloroform, cyclohexane, dichloromethane, dichloroethane, fluorobenzene, heptane, hexanes, toluene, and combinations thereof. In exemplary embodiments, the non-polar solvent may be an alkane, such as for example, pentane, hexane, heptane, cyclopentane, cyclohexane, cycloheptane, or combinations thereof.

The yield of solid sufentanil base can and will vary. Typically, the yield of solid sufentanil base may be at least about 35%. In one embodiment, the yield of solid sufentanil base may range from about 35% to about 65%. In another embodiment, the yield of solid sufentanil base may range from about 65% to about 75%. In yet another embodiment, the yield of solid sufentanil base may range from about 75% to about 85%. In a further embodiment, the yield of the solid sufentanil base may range from about 85% to about 95%. In still another embodiment, the yield of the solid sufentanil base may be greater than about 95%. In an exemplary embodiment, the solid sufentanil base recovered at step (d) may have a yield of at least about 90%.

In various embodiments, the solid sufentanil base recovered at step (d) may contain less than about 5000 ppm of solvent, for example, less than about 4500 ppm, less than about 4000 ppm, less than about 3500 ppm, less than about 3000 ppm, less than about 2500 ppm, less than about 2000 ppm, less than about 1500 ppm, less than about 1000 ppm, less than about 500 ppm, or less than about 100 ppm.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Sufentanil Citrate (IPA+Anhydrous Citric Acid)—Method A

Sufentanil base (1.09 g, 2.81 mmol) was stirred and heated to dissolution (about 35° C.) in 2-propanol (8 mL). Anhydrous citric acid (0.56 g, 2.91 mmol, 1.04 eq.) was added and the mixture further heated to 40° C. to ensure dissolution. The mixture was sterile filtered through an appropriate filter. The reaction mixture was seeded with sufentanil citrate crystals (0.05 mol %) at 40° C. and held at this temperature until crystallization occurred, thereby avoiding an oil phase. The reaction mixture was then cooled to <5° C. and held at this temperature for about 2 hours. The solids were filtered on a Büchner funnnel and washed with 1 mL cold (<5° C.) 2-propanol. After drying in a convection oven at 58-62° C., the product was a white powder (1.47 g, 90.7%). The product typically assayed at 99.29 wt. % with 4600 ppm residual 2-propanol.

Example 2

Sufentanil Citrate (IPA+Anhydrous Citric Acid)—Method B

Sufentanil base (130.71 g, 338.14 mmol) was stirred and heated to dissolution to a temperature of about 72° C. in 2-propanol (378 mL). Anhydrous citric acid (65.66 g, 341.74 mmol) was dissolved in 2-propanol (351.5 mL) and added to the 2-propanol sufentanil base solution with stirring over a period of about 50 minutes. The temperature of the reaction mixture was maintained above at least 62° C. during the addition, then heated to 75° C. and sterile filtered. The reaction was cooled to about 62° C. and seeded with sufentanil citrate (220 mg, 0.38 mmol, 0.001 mol %). The reaction mixture was maintained for 4 hours at 60° C. and then allowed to cool to ambient temperature (about 25° C.) and maintained at ambient temperature for 16 hours with stirring, and then cooled to between about 0° C. and about 5° C. with stirring for about 30 minutes. The reaction mixture containing solid sufentanil citrate was filtered on a Büchner funnel and washed with cold (<5° C.) 2-propanol (125 mL). This procedure yielded white crystals (190.42 g, 97.3%), after vacuum air drying for 3 days on the Bühner funnel. The assay indicated that the material contained between 99 and 101 wt. % sufentanil citrate with <5000 ppm residual 2-propanol.

Example 3

Sufentanil Citrate (IPA+Citric Acid Monohydrate)—Method A

Sufentanil base (1.02 g, 2.63 mmol) was stirred and heated to dissolution (about 35° C.) in 2-propanol (8 mL). Citric acid monohydrate (0.58 g, 2.76 mmol, 1.05 eq.) was added and the mixture further heated to 40° C. to ensure dissolution. The mixture was sterile filtered through an appropriate filter. The reaction mixture was seeded with sufentanil citrate crystals (0.05 mol %) at 40° C. and held at this temperature until crystallization occurred, thereby avoiding an oil phase. The reaction mixture was then cooled to <5° C. held at this temperature for about 2 hours. The solids were filtered on a Büchner funnel and washed with 1 mL cold (<5° C.) 2-propanol. After drying in a convection oven at 58-62° C., the product was a white powder (1.43 g, 93.7%). The product typically assayed at 100.28 wt. % with 4800 ppm residual 2-propanol.

Example 4

Sufentanil Citrate (IPA+Citric Acid Monohydrate)—Method B

Sufentanil base (1.02 g, 2.63 mmol) was charged to a 25 mL three-necked flask with 2-propanol (4 mL) and stirred with a magnetic stirrer. The mixture was heated to 51° C. to dissolve all the sufentanil. Citric acid monohydrate (0.59 g, 2.81 mmol, 1.07 eq.) was charged to a separate flask with 2-propanol (3.9 mL) and stirred to dissolve at ambient temperature, about 22° C. The citric acid solution was added to the sufentanil solution and stirred; the temperature of the combined solution was 39° C. The solution was allowed to cool to ambient temperature while stirring continued; after about 30 minutes the solution became cloudy and the sufentanil citrate slowly came out of solution. The product suspension was cooled in an ice bath for 2 hours (0-5° C.), filtered, and air dried for 2 hours to give sufentanil citrate as a white crystalline solid (1.34 g, 88.2%).

Example 5

Sufentanil Citrate (2-Propanol+Citric Acid Monohydrate)—Method A with Finer Control on Residual 2-Propanol Levels Sufentanil base (13.00 g, 33.63 mmol) and citric acid monohydrate (7.21 g, 34.31 mmol, 1.02 eq) were added to a 250 mL flask equipped with a mechanical stirrer under nitrogen. 2-Propanol (57 mL) was charged to the flask and the slurry was stirred to mix the contents and then heated to dissolve at 80° C. The hot solution was filtered through a 0.45 µm filter and the flask and filter were rinsed with 2-propanol (9 mL). The clear hot solution was cooled to 60°

C. and seeded with sufentanil citrate (20 mg, 0.034 mmol, 0.10 mol %). The cloudy solution was cooled over 1-2 hours to 50° C. and held for 18 hrs. The white slurry was filtered at 50° C. on a Büchner funnel and the solids were washed with 13.0 mL of 2-propanol. The isolated solid was dried at 60° C. to a constant weight in a convection oven. This gave the product as a white powder (17.85 g, 91.7%), 99.86 wt. % assay, with typically 1041 ppm of residual 2-propanol.

Example 6

Sufentanil Citrate (1-Butanol+Citric Acid Monohydrate)

Sufentanil base (1.01 g, 2.61 mmol) was stirred and dissolved 1-butanol (8 mL) at room temperature (about 23° C.). Citric acid monohydrate (0.58 g, 2.76 mmol, 1.06 eq.) was added. The mixture was sterile filtered through an appropriate filter, and the mixture was stirred overnight. The suspension was cooled to <5° C., held for 2 hours and the solids were filtered on a Büchner funnel and washed with 2 mL cold (<5° C.) 1-butanol. After drying in a convection oven at 55-65° C., the product was a white powder (1.44 g, 95.4%). The product typically assayed at 95.69 wt. %.

Example 7

Sufentanil Citrate (2-Butanol+Citric Acid Monohydrate)

Sufentanil base (1.05 g, 2.72 mmol) was stirred in 2-butanol (8 mL) at room temperature. The mixture was heated at 30° C. for 30 minutes to obtain dissolution, filtered and then allowed to cool to room temperature. Citric acid monohydrate (0.60 g, 2.85 mmol, 1.00 eq.) was added and the mixture stirred to ensure dissolution. After about 1 hour at room temperature, crystallization took place. The suspension was stirred overnight, then cooled to <5° C., held for 2 hours and the solids were filtered on a Büchner funnel and washed with 2 mL cold (<5° C.) 2-butanol. After drying in a convection oven at 55-65° C., the product was a white powder (1.43 g, 91.2%). The product typically assayed at 99.85 wt %.

Example 8

Sufentanil Citrate (Ethyl Acetate+Citric Acid Monohydrate)

Sufentanil base (1.04 g, 2.69 mmol) was stirred and heated to dissolution (about 30° C.) in ethyl acetate (8 mL). Citric acid monohydrate (0.62 g, 2.95 mmol, 1.10 eq.) was added and the mixture further heated to from about 76° C. to about 78° C., and held for 1 hour. The suspension was cooled to <5° C. and held for about 0.5 hours. The solids were filtered on a Büchner funnel and washed with 2 mL cold (<5° C.) ethyl acetate. After drying in a convection oven at 58-62° C., the product was a white powder (1.46 g, 93.6%). Product typically assayed at 98.79 wt % with 3100 ppm residual ethyl acetate.

Example 9

Sufentanil Citrate (Isopropyl Acetate+Citric Acid Monohydrate)

Sufentanil base (1.01 g, 2.61 mmol) was stirred and heated to dissolution (about 30° C.) in isopropyl acetate (8 mL). Citric acid monohydrate (0.57 g, 2.71 mmol, 1.04 eq.) was added and the mixture further heated to about 80° C. and held for 1 hour. The suspension was cooled to <5° C. and held for about 0.5 hours. The solids were filtered on a Büchner funnel and washed with 2 mL of cold (<5° C.) isopropyl acetate. After drying in a convection oven at 45-54° C., the product as a white powder (1.27 g, 84.1%). The product typically assayed at 99.54 wt %.

Example 10

Sufentanil Citrate (Methyl Isobutyl Ketone+Citric Acid Monohydrate)

Sufentanil base (1.06 g, 2.74 mmol) was stirred and heated to dissolution (about 30° C.) in methyl isobutyl ketone (8 mL). Citric acid monohydrate (0.61 g, 2.90 mmol, 1.06 eq.) was added. The reaction mixture was filtered if required and then stirred at room temperature overnight. The suspension was cooled to <5° C. and held for about 0.5 hours. The solids were filtered on a Büchner funnel and washed with 2 mL cold (<5° C.) methyl isobutyl ketone. After drying in a convection oven at 55-65° C., the product was a white powder (1.34 g, 84.3%). The product typically assayed at 93.67 wt %.

Example 11

Sufentanil Citrate (Methyl Ethyl Ketone+Citric Acid Monohydrate)

Sufentanil base (1.01 g, 2.61 mmol) was stirred and dissolved methyl ethyl ketone (8 mL) at room temperature. Citric acid monohydrate (0.57 g, 2.71 mmol) was added, crystallization was observed after 5 minutes and the mixture stirred at room temperature overnight. The suspension was cooled to <5° C. and held for about 0.5 hours. The solids were filtered on a Büchner funnel and washed with 2 mL cold (<5° C.) methyl ethyl ketone. After drying in a convection oven at 55-65° C., the product was a white powder (1.47 g, 97.4%). The product typically assayed at 96.27 wt %.

Example 12

Sufentanil Citrate (25% v/v Methanol in Water+Citric Acid Monohydrate)

Sufentanil base (0.97 g, 2.51 mmol) was stirred and heated to dissolution (about 55° C.) in 25% v/v methanol in water (8 mL). Citric acid monohydrate (0.55 g, 2.62 mmol, 1.04 eq.) was added and the mixture cooled. The reaction was cooled to room temperature (crystallization occurred at 35.0° C.). The suspension was stirred overnight. The reaction was then cooled to <5° C., held for 2 hours, then filtered on a Büchner funnel and washed with 2 mL cold (<5° C.) 25% v/v methanol in water. After drying in a convection oven at 55-65° C., the product was white plates (1.20 g, 82.8%). The product typically assayed at 100.26 wt %.

Example 13

Sufentanil Citrate—Water Method 1

Citric acid anhydrous (4.32 g, 22.48 mmol) was dissolved in de-ionized water (30 mL). To this was added sufentanil base (3.00 g, 7.76 mmol, 0.34 eq) and then mixed to dissolution at 75-85° C. The mixture was filtered then cooled to room temperature, the product crystallized thereafter within 3 hours. The mixture was then cooled to 0-5° C. and held for 1-3 hours. The mixture was filtered on a Büchner funnel and washed with water (4 mL). The wet cake was dried in a vacuum oven (~200 mbar, 55-60° C. with a nitrogen sweep for 16 hours. This gave the product as a white powder (3.60 g, 80.2%), with 99.09 wt. % assay.

Example 14

Sufentanil Citrate—Water Method 2

In Reactor 1, citric acid anhydrous (10.46 g, 54.44 mmol, 2.81 eq.) was dissolved in deionized water (53 mL). Sufentanil base (7.50 g, 19.40 mmol) was charged and the reaction placed under nitrogen, heated until all the solids dissolved (75-80° C.), and filtered. The filter was rinsed forward with deionized water (7.0 mL). The reaction was stirred and allowed to cool to ambient temperature (about 23° C.). The system was heated to 76.9° C. to redissolve the solids; the temperature was reduced then to 42-44° C., which resulted in the solution becoming cloudy within 1.2 hours and a thick slurry of crystalline sufentanil citrate developed within 1.8 hours. No stickiness or gumminess was observed under these conditions. The sufentanil citrate/water slurry was cooled and held at about 14° C.

In Reactor 2, citric acid anhydrous (21.37 g, 111.2 mmol, 1.01 eq.) was dissolved in de-ionized water (350 mL). Sufentanil base (42.52 g, 110.0 mmol) was added, the mixture was placed under nitrogen, heated and stirred to dissolve the solids (95-98° C.), and filtered. The filter was rinsed forward with 50 mL of deionized water into the batch. The hot sufentanil citrate solution (the contents of Reactor 2) was added over a period of about 1 hour to the cooled aqueous sufentanil citrate slurry (Reactor 1) with vigorous stirring, such that the temperature was maintained between 17.5° C. and 18.5° C. After the addition was complete, the reaction mixture was stirred at ambient temperature overnight and then cooled to 2.7° C. for 1 hour. The sufentanil citrate was recovered by filtration, washed with cold deionized water (50 mL), air-dried for 16 hours, then dried in a vacuum oven (100-200 mbar, 56-62° C. with a nitrogen sweep) for 16 hours. This procedure gave sufentanil citrate as a white powder (66.19 g, 88.4%). The mother liquors were reserved for recovery of the sufentanil base.

Example 15

Sufentanil Base (from Sufentanil Citrate Mother Liquors)

The combined mother liquor and aqueous cake washes from the preparation of sufentanil citrate (Example 12, about 460 mL) were pH-adjusted from 2.83 in steps to 5.03 and 6.04 with 50% w/w aqueous sodium hydroxide. After 0.5 hours at a pH of about 6, the solution became cloudy, a more dilute solution of base (15% w/w) was used to adjust the pH to 7.37 and then to 12.11. The suspension was cooled on an ice bath to 2.6° C. for approximately 1 hour and the sufentanil base was recovered by filtration. The sufentanil base was air-dried for 16 hours and dried in a vacuum oven (100-200 mbar, 56-62 ° C. with a nitrogen sweep) for 16 hours. This procedure gave recovered sufentanil base as a white powder (4.97 g, 9.9% recovery based on 50.02 g of total sufentanil base charged in Example 12).

Example 16

Sufentanil Base (from Sufentanil Citrate)

Sufentanil citrate (65.40 g, 113.0 mmol) was mixed with ethanol (128 mL) and deionized water (200 mL), and then heated to dissolution (about 35° C.). The pH of this solution was adjusted to >12.5 by the addition of 50% w/w aqueous sodium hydroxide, and then cooled to <5° C. in an ice bath. The product was filtered and washed with cold deionized water (about 20 mL). The crude sufentanil base was air-dried then dissolved in n-heptane (146 mL) at about 75° C., with any residual water removed using a Dean-Stark trap. The hot n-heptane solution was passed through a bed of decolorizing carbon (Darco™, 2.00 g) supported on bleached diatomaceous earth (Celite™, 2.00 g) and allowed to cool room temperature followed by cooling to 0-5° C. The sufentanil base was obtained by filtration of the white prisms on a Büchner funnel followed by washing with 2 mL cold (<5° C.) n-heptane. After air-drying, sufentanil base was white needles (43.46 g, 99.5%). The product typically assayed at 100.40 wt. %.

What is claimed is:

1. A process for preparing sufentanil citrate from sufentanil base, the process comprising:
   (a) forming a reaction mixture comprising sufentanil base, citric acid, and isopropyl alcohol;
   (b) heating the reaction mixture to a temperature of 70° C. to 90° C. to form a solution comprising sufentanil citrate;
   (c) cooling the solution comprising sufentanil citrate to 50° C. to 70° C., seeding with crystals of sufentanil citrate, and maintaining the temperature at 50° C. to 60° C. thereby forming a slurry, the slurry comprising solid sufentanil citrate; and
   (d) maintaining the temperature of the slurry at 50° C. to 60° C. and filtering the slurry at 50° C. to 60° C. to recover the solid sufentanil citrate, which contains less than about 2000 ppm of isopropyl alcohol.

2. The process of claim 1, further comprising:
   (e) contacting the mixture remaining after recovery of solid sufentanil citrate with a proton acceptor to form a sufentanil base mixture;
   (f) cooling the sufentanil base mixture to form solid sufentanil base; and
   (g) recovering solid sufentanil base.

3. The process of claim 2, further comprising contacting solid sufentanil base from step (g) with a non-polar solvent to form a mixture, heating the mixture to dissolve the sufentanil base, and cooling the mixture to form crystalline sufentanil base.

4. The process of claim 3, wherein the proton acceptor comprises a hydroxide and the non-polar solvent is an alkane.

* * * * *